(12) United States Patent
Gidekel et al.

(10) Patent No.: US 7,622,109 B2
(45) Date of Patent: Nov. 24, 2009

(54) PLANT GENE AND USES THEREOF

(75) Inventors: Manuel Gidekel, Temuco (CL); Ana Gutierrez, Temuco (CL); Claudia Rabert, Temuco (CL); Gustavo Gabrera, Temuco (CL); Jaime Sanchez, Temuco (CL); Leon Bravo, Comuna de Coronel (CL)

(73) Assignees: Vitrogen SA, Santiago (CL); Universidad de la Frontera, Temuco (CL)

( * ) Notice: Subject to any disclaimer, the term of this patent is extended or adjusted under 35 U.S.C. 154(b) by 0 days.

(21) Appl. No.: 12/316,988

(22) Filed: Dec. 18, 2008

(65) Prior Publication Data

US 2009/0117062 A1    May 7, 2009

Related U.S. Application Data

(62) Division of application No. 11/787,383, filed on Apr. 16, 2007, now Pat. No. 7,485,445.

(51) Int. Cl.
*A61K 38/46* (2006.01)
(52) U.S. Cl. .................. 424/94.6; 435/198; 435/252.3; 435/320.1; 536/23.2
(58) Field of Classification Search ................ 424/94.6; 435/198, 252.2, 320.1; 536/23.2
See application file for complete search history.

(56) References Cited

U.S. PATENT DOCUMENTS 6,551,607 B1 *   4/2003   Minerath et al. ............ 424/402

* cited by examiner

*Primary Examiner*—Tekchand Saidha
(74) *Attorney, Agent, or Firm*—Dodds & Associates; L. Susanne Somersalo; John Dodds

(57) ABSTRACT

A novel gene isolated from *Deschampsia antarctica* coding for a lipase like protein is disclosed. A system for production of recombinant enzyme is also disclosed as well as use for the enzyme in sunscreen.

9 Claims, 9 Drawing Sheets

> gi|51038104|gb|AAT93907.1| putative GDSL lipase/acylhydrolase [Oryza sativa (japonica cultivar-group)]
gi|55168051|gb|AAV43919.1| putative GDSL lipase/acylhydrolase [Oryza sativa (japonica cultivar-group)]
Length=101

Score = 84.7 bits (208), Expect = 1e-15
Identities = 56/101 (55%), Positives = 70/101 (69%), Gaps = 4/101 (3%)
Frame = +1

Query  1    MFAIKYGFVANHTKYGIEWPLMVCCgngppynfnpgkfgCG---DLCGPEARVLSMDGV  171
            MFAIKY  VANHTK+GIE PLM CCG+GGPPYN++P K     DLC     + +SWDGV
Sbjct  1    MFAIKYDLVANHTKHGIEKPLMTCCGHGGPPYNYDPKKSCTANDKDLCKLGEKFISWDGV  60

Query  172  HFTDFGSGLAAKHVMSGEYSKPRVKL-ASLINGGSKKSSSL  291
            HFTD  + A  V+SGE+S PR+KL AS++     K+S L
Sbjct  61   HFTDAANEIVASKVISGEFSIPRIKLTASVVRPKKAKNSRL  101

Fig. 1

```
                                                                                          Section 1
          (1)  1         10        20        30        40        50        60
    Da   (1)  MFAIKYGFVANETKNGIEWPLMVCCGNGGPPYNENPGK---FGCGDLCGPEARVESWDGVHFTDFGSGEAAKH
    Os   (1)  MFAIKYDLVANETKHGIEKPLMTCCGHGGPPYNYDPKKSCTANDKDLCKLGEKFESWDGVHFTDAANEIVASK
Consensus (1)  MFAIKY  VANHTKEGIE PLM CCG GGPPYNF P K         DLC   K ISWDGVHFTD A  I A
                                                                                          Section 2
          (77) 77        90        101
    Da   (74) GEYSKPRVKLASLINGGSKKSSSL-
    Os   (77) GEFSIPRIKLTESVVRPKKAKHSRL
Consensus (77) GEFS PRIKL A I       K  S
```

FIG. 2

```
                                                                                          Section 1
         (1)  1         10        20        30        40        50        60
Da       (1)  ------------------------------------------------------------
Os       (1)  ------------------------------------------------------------
At       (1)  ---------GDSNSDTGGLVAGLGYPIGFPNGRLFFRRSTGRLSDGRLLIDFLCQSLNTSLLRPYLDSLGRT
CaA      (1)  MRVSLRSITSLLAAATAAVLAAPAAETLDRRAALPNPYDDPFYTTPSNLGTFAKGQVIQSRKVPTDLGNANNA
CaB      (1)  --------MKLLSLTGVAGVLATCVAATPLVKRLPSGSDPAFSQPKSVLDAGLTCQGASPSSVSKPLLLVPGT
Consensus(1)               S   ALA                             L         Q     V  I
                                                                                          Section 2
        (77)  77        90       100       110       120       130       140
Da       (1)  ------------------------------------------------------------
Os       (1)  ------------------------------------------------------------
At      (67)  NVANFAIAGSSTLPKNVPFSLNIQVKQFSH--FKSRSLELASSSNSLKGMFISNNGFKNALYMIDIGQNDLAI
CaA     (77)  QLQYRTTNTQNEAVADVATVWIPAKPASPPKIFSYQVYEDATALDCAPSYSYLTGLDQPNKVTAVLDTPILIG
CaB     (69)  GPQ---SFDSNWIPLSTQLGYTPCWISPPP--FMLNDTQVNLEYMVNAITALYAGSGNNKLPVLTWSQGGLVA
Consensus(77)                                  F          T                             I
                                                                                          Section 3
       (153) 153       160       170       180       190       200       210
Da       (1)  ------------------------------------------------------------
Os       (1)  ------------------------------------------------------------
At     (141)  RGNSYSQTVKLIPQIITEIKSSIKRLYDEEGRRFWIHNTGPLGCLPQKLSMVKSKDLDQLGCLVSYNSALTLF
CaA    (153)  QQGYYVVSSDHEGFKAAFIAGYEEGMAILDGIRALKNYQNLPSDSKVALEGYSGGAHATVWATSLAESYAPEI
CaB    (140)  LTFFPSIRSKVDRLMAFAPDYKGTVLAGPLDALAVSAPSVWQQTTGSALTTALRNAGGLTQIVPTINLYSATI
Consensus(153)                          L                    L                      A
                                                                                          Section 4
       (229) 229       240       250       260       270       280       290
Da       (1)  ---------------------------MFAIKYGFVANHTKYGLEWPLMVCCG------NGG------PP
Os       (1)  ---------------------------MFAIKYDLVANHTKHGLEKPLMICCG------HGG------PP
At     (217)  LDHMCEELRTELRDATIIY------IDLYAIKYSLLANSNQLGFKSPLMACCG------YGG------TP
CaA    (229)  GASHGGTPVSAKDTFTFLNGGPFAGFALAGVEGLSLAHPDMESFIEARLNAKGQRTLKQIRGRGFCLPQVVLT
CaB    (216)  QPQVSNSPLDSSYLFNGKN------VQAQAVCGPLFVIDHAGSLTSQFSYVVG------RSL------LR
Consensus(229)                            MFAIKY LVAN  YGI  PLM CCG       GG        PI
```

FIG. 4.

```
                                                                                          Section 5
         (305)  305      310        320       330       340        350       360       370
    Da   (35)  NPGK---FGCGDLCGPEARVISWDGVHETDFGSGLAAKHVMSG--EYSKPRVKHASLINGGSKKSSSL-----
    Os   (35)  DPKKSCTANDKDLCKLGEKFISWDGVHETDAANEIVASKVISG--EFSIPRIKLTASVVRPKKAKNSRL----
    At  (272)  NVKIICGHKGSMVCKEGSRFISWDGIHYTG--------------------------------------------
    CaA (305)  LNVFSLVNDTNLLNEAPIASILKQETVVQAEMSYIVSVPKFPRFIWHAIPDEIMPYQPAATYVLEQCAKGANI
    CaB (271)  GQARSADYGITDCNPLPANDLTPEQKVAAAALLAPAAAAEVAGPKQNCEPDLMPYARPFAVGKRICSGIVTP-
Consensus (305)        KS         DLC    AR ISWDGVHFTA A      A    VISG    S PI L A   A K   S
                                                                                          Section 6
         (381) 381       390       400       410       420       430       440
    Da   (96)  --------------------------------------------------------------------------
    Os  (102)  --------------------------------------------------------------------------
    At  (302)  --------------------------------------------------------------------------
    CaA (381)  PYPIAEHLTAEIFGLVPSLWFIKQAFDGTTPKVICGTPIPAIAGITTPSADQVLGSDLANQLRSLDGLQSAFGH
    CaB (343)  --------------------------------------------------------------------------
Consensus (381)
                                                                                          Section 7
         (457) 457   462
    Da   (96)  ------
    Os  (102)  ------
    At  (302)  ------
    CaA (457)  GPITPP
    CaB (343)  ------
Consensus (457)
```

FIG. 4

1,2-o-Dilauryl-rac-glycero-3-glutaric acid (6-methylresorufin)ester
Lipase/Colipase 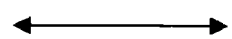
1,2-o-Dilauryl-rac-glycerin + Glutaric acid (6-methylresorufin)-ester
spontaneous degradation
Glutaric acid (6-methylresorufin)-ester ⟷ Glutaric acid + Methylresorufin
FIG 6

PLANT GENE AND USES THEREOF

PRIORITY DATA

This application is a divisional application of U.S. non provisional application Ser. No. 11/787,383 filed on Apr. 16, 2007.

SEQUENCE DATA

This application contains sequence data provided on a computer readable diskette and as a paper version. The paper version of the sequence data is identical to the data provided on the diskette.

This application is a division of U.S. Ser. No. 11/787,383, filed Apr. 16, 2007, now U.S. Pat. No. 7,485,445.

BACKGROUND OF THE INVENTION

1. Field of the Invention

The present invention relates generally to the field of plant molecular biology. More specifically the invention relates to nucleic acid fragment encoding plant lipase and its use as sunscreen component.

2. Description of Related Art

Lipases (triacylglycerol acylhydrolase, EC 3.1.1.3) belong to the family of hydrolases that act on carboxylic ester bonds. In addition to their natural function of hydrolyzing carboxylic ester bonds, lipases can catalyze esterification, interesterification, and transesterification reactions in non aqueous media. Due to this versatility lipases have a variety of potential applications for industrial uses. Examples of fields where lipases have applications are such as dairy industry, detergents, oleo chemical industry, pharmaceutical and cosmetic industry, medical and environmental applications. Depending on the process, the required characteristics of the lipase enzymes are different. For purposes where for example processing temperatures are high, one would need to have enzyme with high optimal temperature, for another process one may need to have an enzyme having low pH tolerance etc. Moreover, the modern biotechnology has enabled production of industrial enzymes such as lipases cell cultures, whereby the production costs can be dramatically lowered.

GDSL lipases are an important family of lipases. GDSL lipases are widely found in microbes, and a number of bacterial GDSL genes have been cloned and characterized. GDSL lipases are also found in plant species, and several candidates from various plant species such as *Arabidopsis thaliana, Rauvolfia serpentina, Medigago sativa, Hevea brasiliensis, Brassica napus, Oryza sativa* and *Alopecurus myosuroides* have been isolated, cloned and characterized.

Due to the large variety of industrial uses where lipase enzymes can be used, there is a clear need to identify and characterize new enzymes and genes coding for them and to provide systems for industrial production of the enzymes.

Accordingly, identification and characterization of genes coding for lipase like proteins in plant species tolerant to low temperatures can provide novel enzymes for industrial applications. A plant species extremely tolerant to low temperatures is *Deschampsia antarctica* Desv. (Poacea). Accordingly, we have studied the gene expression of this vascular plant naturally colonizing Maritime Antarctic Peninsula.

SUMMARY OF THE INVENTION

Due to the increased interest in lipases in various fields of industry, there is a clear need for novel lipase enzymes. Especially, there is a need for novel lipase enzymes functional in wide range of temperatures. Moreover, there is a need for a method for economic production of lipase enzymes.

Accordingly, an object of the current invention is to provide a novel recombinant lipase, which is psycrophilic and can therefore stand low temperatures.

Another object of the current invention is to provide a simple and rapid method of producing lipase enzyme in host cell and subsequent purification of recombinant lipase.

An even further object of the current invention is to provide a novel lipase that can be used in waste water cleaning.

A further object of the current invention is to provide a novel lipase to be used as a component in sun screens.

According to a preferred embodiment the lipase enzyme is encoded by a nucleotide sequence essentially according to SEQ ID NO: 1 isolated from *Deschampsia antarctica*.

In a preferred embodiment, lipase enzyme of the present invention comprises the amino acid sequence essentially according to SEQ ID NO: 2.

Yet another embodiment of the present invention is a chimeric gene comprising an isolated nucleotide sequence encoding lipase like protein of *Deschampsia antarctica*.

An even further embodiment of the present invention is isolated host cells comprising the chimeric gene. The host cell may be eukaryotic, such as yeast or a plant cell, or it may be prokaryotic such as a bacterial cell. According to one embodiment the host cell comprising the chimeric gene is a *Pichia* cell.

An even further embodiment of the instant invention is to provide a process for cultivating host cells comprising the chimeric gene and isolating the recombinant enzyme produced in the cells.

Yet another embodiment of the instant invention is to provide a lipase enzyme for purposes of waste water cleaning.

An even further embodiment of the instant invention is to provide a sunscreen comprising the plant lipase of this invention.

BRIEF DESCRIPTION OF THE DRAWINGS

FIG. 1. shows the BLAST analysis of lipase clone 3F9 (SEQ ID NO: 2) with a putative GDSL lipase/acylhydrolase of *Oryza sativa* (japonica cultivar-group) (SEQ ID NO:6).

FIG. 2. illustrates a comparison of *Deschampsia antarctica* (Da) (SEQ ID NO:1) and *Oryza sativa* (Os) lipase protein-encoding gene (SEQ ID NO:6) showing the consensus region.

FIG. 4 shows an alignment of *Deschampsia antartica* lipase (SEQ ID NO: 2) with previously cloned lipases using the Vector NTI 7 software. *Deschampsia antarctica* lipase 3F9 (Da) (SEQ ID NO:2), putative GDSL lipase/acylhydrolase of *Oryza sativa* (Os) (SEQ ID NO:6), lipase homolog of *Arabidopsis thaliana* (At) (SEQ ID NO:7), lipase A (CaA) (SEQ ID NO:8) and lipase precursor B (CaB) of *Candida antarctica* (SEQ ID NO:9) and consensus region.

FIG. 6 shows the reaction sequence employed in the commercial kit to measure lipase activity in *P. pastori* cell culture.

DETAILED DESCRIPTION OF THE INVENTION

A cDNA expression library was obtained by using DNA samples of *Deschampsia antarctica*. This library enabled identification of one gene which encoded a lipase-like enzyme (triglyceride lipases EC 3.1.1.3). The cDNA gene sequence encoding the lipase of *Deschampsia antarctica* is according to SEQ ID NO: 1.

This full length gene sequence was further compared with other gene sequences available in a public GeneBank (BLAST). The clone 3F9 showed homology (69% positive) with a putative GDSL lipase/acylhydrolase of *Oryza sativa* (japonica cultivar-group) having the sequence identified as AAT93907.1. The comparison is shown in FIG. 1.

The alignment of lipase 3F9 clone with the putative GDSL lipase/acylhydrolase of *Oryza sativa* (japonica cultivar-group) gene was conducted by using the Vector NTI 7 software. The amino acid sequence for both lipases showed a 52.5% identity and 63.4% similarity (FIG. 2). This clearly indicates that the plant lipase gene of this disclosure is novel.

Figure 3:
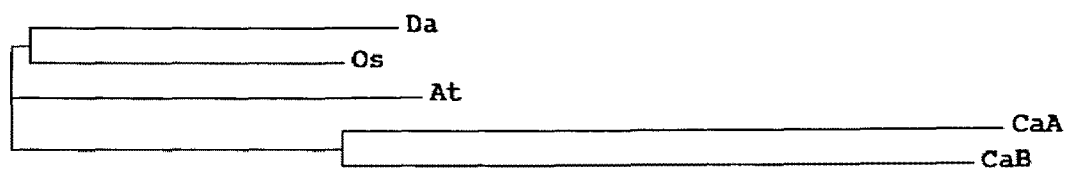
FIG. 3. depicts a phylogenetic tree displaying the inherited relationships between lipase 3F9 of *Deschampsia antarctica* (Da), putative GDSL lipase/acylhydrolase of *Oryza sativa* (Os), lipase homolog of *Arabidopsis thaliana* (At), lipase A (CaA) and lipase precursor B (CaB) of *Candida antarctica*.

A phylogenetic analysis of several plant and bacterial lipases was carried out in order to illustrate the presumed evolutionary relationships among them and to infer their evolutionary history. For this purpose, the lipase 3F9 of *Deschampsia antarctica* (Da), putative GDSL lipase/acylhydrolase of *Oryza sativa* (Os), lipase homolog of *Arabidopsis thaliana* (At), lipase A (CaA) and lipase precursor B (CaB) of *Candida antarctica* (FIG. 4) were compared. Finally, a phylogenetic tree was built (FIG. 3). It was found that there was no phylogenetic relationship between *Deschampsia antarctica* lipase 3F9 and lipase homolog of *Arabidopsis thaliana*, lipase B precursor and lipase A of *Candida antarctica*. The only phylogenetically related protein is the *Oryza sativa* lipase, which was previously demonstrated having only a 63.4% of similarity.

In order to assure that *Deschampsia antarctica* 3F9 protein is novel a further comparison with functional related lipases was conducted by using a GenBank information. The simultaneous alignment of *D. antractica* lipase 3F9, putative GDSL lipase/acylhydrolase of *Oryza sativa*, lipase homolog of *Arabidopsis thaliana*, lipase B precursor and lipase A of *Candida antarctica* are shown in FIG. 4. The amino acid sequence of lipase 3F9 of *Deschampsia antarctica* showed 52.5% identity with lipase protein of *Oryza sativa*, 8.3% identity with lipase protein of *Arabidopsis thaliana*, only 2.4% identity with *Candida antarctica* chain A and 4.1% identity with *Candida antarctica* chain B.

The molecular weight of 3F9 lipase of *D. antarctica* is 10.3 kDa, while the molecular weight of lipase of *O. sativa* is 11.1 kDa, and that of *A. thaliana* is 33.3 kDa. The isoelectric point of 3F9 lipase of *D. antarctica* is 8.99, while that of lipase of *O. sativa* is 9.26 and the isoelectric point of lipase of *A. thaliana* is 9.20. Thus, clearly also the biochemical characterization of the instant plant lipase is distinct from the known proteins with similar function. The results from the sequence comparison and the biochemical analysis are summarized in Tables 1 and 2.

TABLE 1

Identity comparison of the amino acid sequence of lipase 3F9 of *D. antarctica* with other lipases.

| | *Deschampsia antarctica* (Da) | |
|---|---|---|
| | Similarity (%) | Identity (%) |
| *Oryza sativa* (Os) | 63.4 | 52.5 |
| *Arabidopsis thaliana* (At) | 11 | 8.3 |
| *Candida antarctica* chain A (CaA) | 5.4 | 2.4 |
| *Candida antarctica* chain B (CaB) | 8.2 | 4.1 |

TABLE 2

Biochemical comparison of lipase properties isolated from different sources.

| | Molecular Weight KDa | Isoelectric point |
|---|---|---|
| *Deschampsia antarctica* (Da) | 10.3 | 8.99 |
| *Orysa sativa* (Os) | 11.1 | 9.26 |
| *Arabidopsis thaliana* (At) | 33.3 | 9.20 |
| *Candida antarctica* chain A (CaA) | 49.2 | 5.33 |
| *Candida antarctica* chain B (CaB) | 33 | 5.80 |

The amino acid sequence of *Deschampsia antarctica* lipase deduced from DNA sequence is according to SEQ ID NO: 2. The amino acid composition of the lipase protein encoded by DNA sequence is presented in Table 3.

TABLE 3

Amino acid composition of *Deschampsia antarctica* lipase deduced from DNA sequence.

| Amino Acid(s) | Number count | % by weight | % by frequency |
|---|---|---|---|
| Charged (RKHYCDE) | 27 | 33.36 | 27.84 |
| Acidic (DE) | 6 | 6.95 | 6.19 |
| Basic (KR) | 10 | 12.55 | 10.31 |
| Polar (NCQSTY) | 24 | 25.26 | 24.74 |
| Hydrophobic (AILFWV) | 30 | 32.66 | 30.93 |
| A Ala | 6 | 4.42 | 6.19 |
| C Cys | 4 | 4.01 | 4.12 |
| D Asp | 3 | 3.30 | 3.09 |
| E Glu | 3 | 3.65 | 3.09 |
| F Phe | 6 | 8.20 | 6.19 |
| G Gly | 15 | 9.31 | 15.46 |
| H His | 3 | 3.85 | 3.09 |
| I Ile | 3 | 3.25 | 3.09 |
| K Lys | 8 | 9.67 | 8.25 |
| L Leu | 7 | 7.59 | 7.22 |
| M Met | 3 | 3.70 | 3.09 |
| N Asn | 5 | 5.46 | 5.15 |
| P Pro | 6 | 5.71 | 6.19 |
| Q Gln | 0 | 0.00 | 0.00 |
| R Arg | 2 | 2.88 | 2.06 |
| S Ser | 9 | 7.82 | 9.28 |
| T Thr | 2 | 1.97 | 2.06 |
| V Val | 6 | 5.81 | 6.19 |
| W Trp | 2 | 3.38 | 2.06 |
| Y Tyr | 4 | 5.99 | 4.12 |
| B Asx | 8 | 8.77 | 8.25 |
| Z Glx | 3 | 3.65 | 3.09 |
| X Xxx | 0 | 0.00 | 0.00 |

The present invention is now further defined in the following examples. It should be understood that these examples, while indicating preferred embodiments of the invention, are given by way of illustration only. It would be apparent to one skilled in the art that various modifications of the invention in addition to those shown and described herein are within the scope of the invention.

Example 1

Strains, Vectors and Culture Media

*Escherichia coli* strain DH5α (Invitrogen) was selected for vector construction and *Pichia pastoris* strain X-33 (Invitrogen) was used to express the *Deschampsia antarctica* lipase 3F9. *E. coli* was grown in low salt LB-Zeocin medium (1% tryptone, 0.5% yeast extract, 0.5% NaCl and 25 µg/ml of zeocin).

*Pichia pastoris* was grown in YPD medium (1% yeast extract, 2% peptone, 2% dextrose) for general growth and storage and in BMGY medium (1% yeast extract, 2% peptone, 100 mM potassium phosphate, pH 6.0, 1.34% YNB, $4\times10^{-5}$% biotin, 1% glycerol) or in BMMY medium (1% yeast extract, 2% peptone, 100 mM potassium phosphate, pH 6.0, 1.34% YNB, $4\times10^{-5}$% biotin, 0.5% methanol) to generate biomass or to induce expression, respectively. Zeocin 100 µg/ml agar plates were used (1% yeast extract, 2% peptone, 2% dextrose, 2% agar, 100 µg/ml zeocin) for selection of the transformants.

The *P. pastoris* X-33 and pPICZαB, used as fungal host and expression vector were purchased from Invitrogen Corporation.

Example 2

Vector Construction and Transformation

Figure 5:
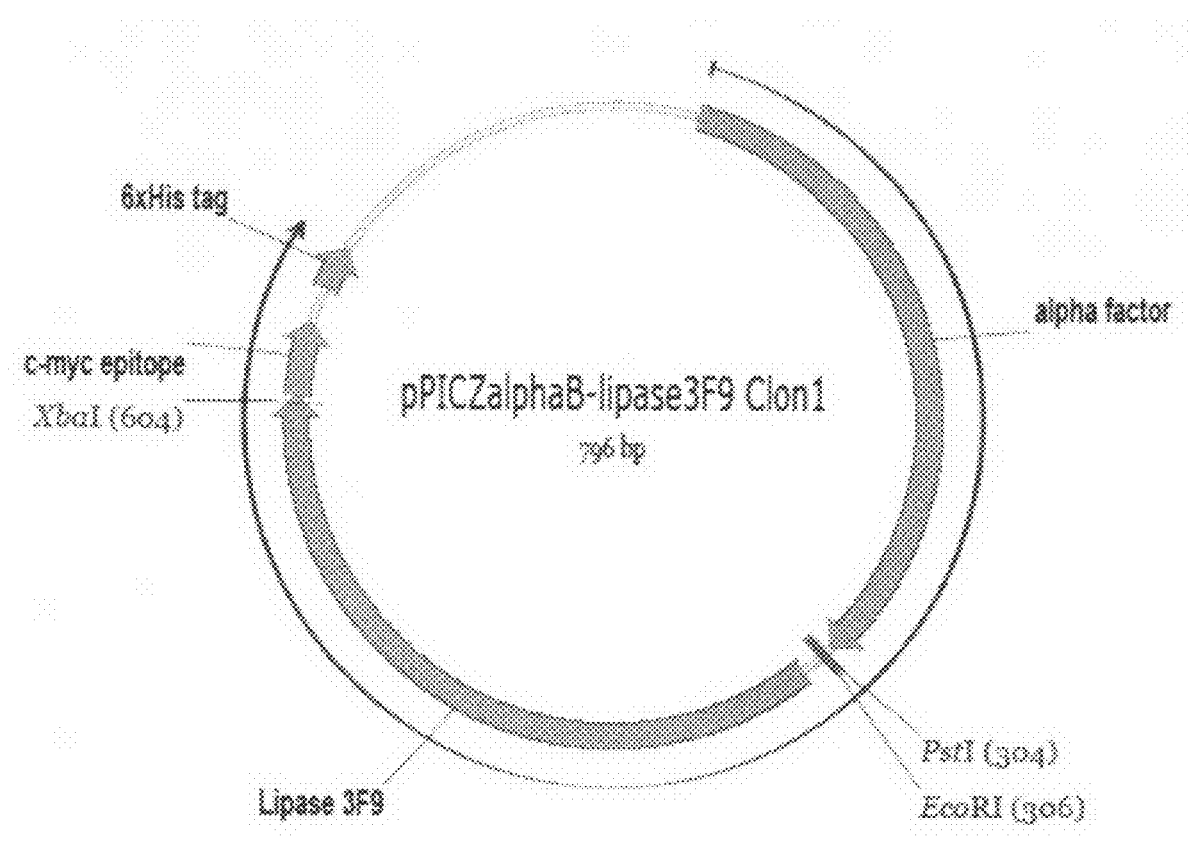
FIG. 5 depicts the expression vector pPICZalphaB-Lipase 3F9 Clon1 of *Deschampsia Antarctica*, the ORF with the alpha factor (secretor signal) and the 6×His tag to facilitate the protein purification.

The *Deschampsia antarctica* lipase 3F9 gene was isolated by polymerase chain reaction (PCR) amplification using de primers fw3F9 (5'CATGTTCGCCATCAAGTACG) SEQ ID NO: 3 and rev3F9 (5' TCTAGAGATGATGATTTCTTG-GAGC) SEQ ID NO: 4. This introduced an XbaI of the gene. PCR fragments were purified and DNA fragments were recovered from agarose gels using Ultra Clean 15 DNA purification Kit (Carlsbad, Calif., USA). DNA was purified and manipulated essentially as described by Sambrook et al., 1989. The PCR product was cloned into pGEM-T Easy (Promega) and liberated with the enzymes EcoRI and XbaI and ligated to the vector pPICZαB digested with the same restriction enzymes. This resulted in the expression vector pPICZalphaB-Lipase 3F9 Clon1 (FIG. 5). All amplifications by PCR were performed by using Taq DNA Polymerase recombinant LC (Fermentas, Hanover, USA).

The resulting plasmid constructs were transformed into *E. coli* and transformants were selected on low salt LB-Zeocin. The plasmid recombinant DNA was sequenced with 5-AOX1 promoter primer (5' GACTGGTTCCAATTGACAAGC) SEQ ID NO: 5 which annealed with the pPICZαB sequence. Sequence alignment was performed by BLAST.

Example 3

Lipase Expression in *P. pastoris*

Electrocompetent cells of *P. pastoris* X-33 were prepared according to the supplier's instruction (Invitrogen). Ten micrograms recombinant plasmid linearized with PmeI was mixed with 80 µl electrocompetent cells and electroporated by means of pulse discharge (1500 V, 25 F, Bio-Rad Gene Pulser) for 5 ms. After pulsing, 1 ml ice-cold 1M sorbitol was immediately added to the cuvette. Then, 200 µl aliquots were spread on YPDS plates (1% yeast extract, 2% peptone, 2% dextrose, 1M sorbitol, 2% agar, 100 µg/ml zeocin), and the plates were incubated at 30° C. to screen for zeocin resistant transformants according to their capacity to grow in the presence of zeocin. Resistant zeocin clones were grown on BMGY medium at 30° C. over night until $OD_{600}$=2-6 then transferred onto BMMY medium. Methanol was added to the culture medium to a final concentration of 0.5% (v/v) every 24 h to induce the lipase protein expression.

Example 5

Induction of Lipase Production

Culture grown in BMGY for 96 hr was transferred into BMMY medium for induction of the inserted gen. Methanol was added to the culture medium to a final concentration of 0.5% (v/v) every 24 h for the following 3 days. The sample was collected by separating the culture medium by filtration and concentration of the culture broth. One aliquot of the sample was taken and lipase activity was measured using the commercial kit (Lipase DC FS (Diagnostic Systems International). The kit is based on the use of a synthetic substrate for lipase, which generates a colored product whose formation is evaluated in thermoregulated spectrophotometer at 580 nm (FIG. 6).

Figure 7:
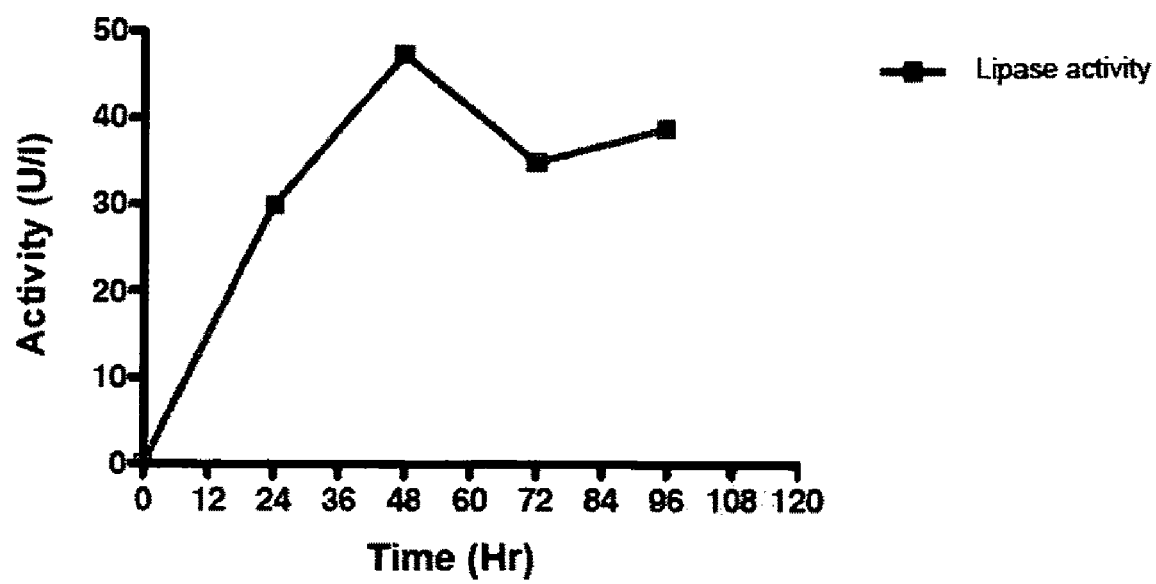
FIG. 7 illustrates the determination of lipase activity (U/L) at different induction times with methanol in *P. pastoris* broth.

FIG. 7 illustrates induction of the inserted gene in *P. pastori* (encoding the Da lipase enzyme production) by adding methanol to the broth culture. The maximum induction was reached at 48 h.

Example 6

Lipase Activity at Different Temperatures

Figure 8:
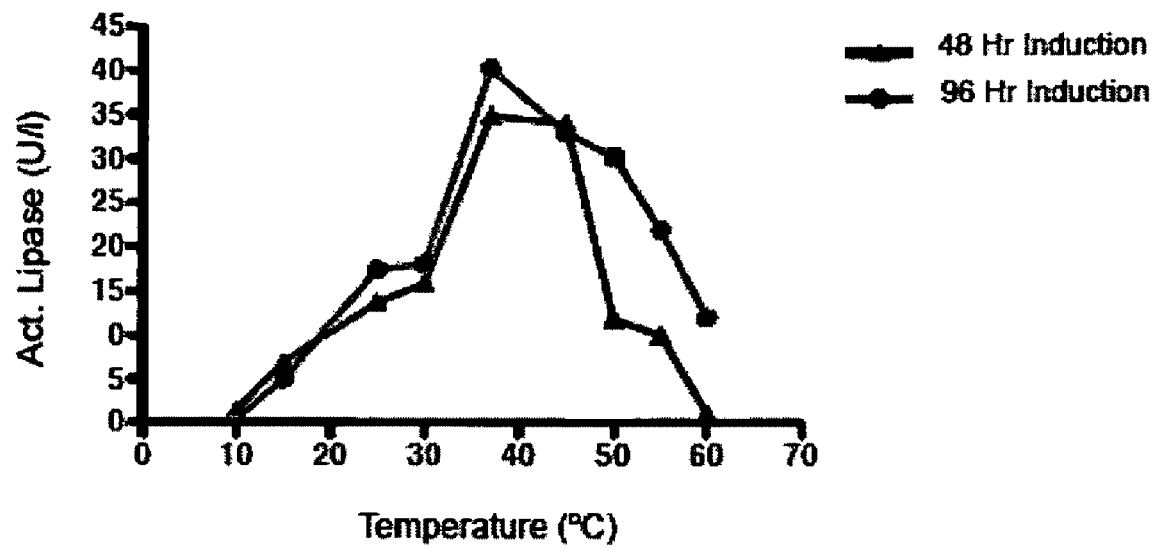
FIG. 8 illustrates lipase activity (U/L) at different temperature at 48 hours and 96 hours induction period.

Assay to determine the optimum temperature of *Deschampsia antarctica* cloned lipase was conducted next. Supernatant samples were removed from the induced media to measure the lipase activity. The activity was measured in a thermoregulated spectrophotometer at 580 nm in a temperature range from 11° C. to 60° C. The assays were run for two different induction times, 48 hours and 96 hours (FIG. 8). The maximum lipase activity was observed at 35-45° C. 50% of the activity was lost at 25° C. This behavior is characteristic of a psychrophilic enzyme.

Example 7

Composition of a Sun Screen

Lipase enzymes are known to catalyze transesterification reaction resulting to ferulyl or coumaryl-substituted acylglycerols. Such acylglycerols are known to be efficient as sun screen agents.

The lipase enzyme according to the present invention is psycrophilic, i.e. it has low optimal temperature and at ambient temperatures it clearly has a high activity. Based on this characteristic one preferred embodiment of the instant invention is to use the novel lipase enzyme as a compound in sun screen lotion. Other components of the lotion would comprise triglycerides from natural origin, antioxidant compound that could act as photoreceptors and having at least one carboxyl group on its structure and other compound necessary for a spray formulation. Examples of triglycerides are glycerine, coconut oil, olive oil, rapeseed oil among others. The photoreceptor agent could be for example cinnamic acid, ferulic acid, quinic acid, shikimic acid, or the other antioxidants from

*Deschampisa antarctica*. Any of the isolated optical stereoisomer, or derivatives as well as their mixtures, can be used in the composition of the invention. As the psycrophilic lipase is able to react under very mild conditions (FIG. 8)) it will initiate the esterification reaction between natural oils and photoreceptor once the lotion in sprayed on the skin and the sunlight UV-B rays reaches it.

Example 8

Use of the Lipase Enzyme in Waste Water Cleaning

The lipase enzyme according to this disclosure can be used in a method for the continuous treatment to clean wastewater coming from different sources, mainly containing oil, fats waxes or any esterified compounds present during mil processing, soap producing, tannin industry and other related industries in a treatment plant. Such method comprises the steps of: a) providing a mixture comprising active amounts of an enzyme comprising a psycrophilic lipase (immobilized or not); b) immersing said mixture in fresh water for about 1 hour to about 3 hours at water temperature (ranging from 4 to 20° C.) in order to provide an activated mixture; c) mixing a volume of aqueous water waste from said treatment plant with a volume of said enzyme from about 2 hours to about 48 hours at room temperature to produce an acclimated mixture; d) adding a volume of said acclimated mixture to a wastewater treatment tank in said treatment plant and; e) maintaining said mixture and said wastewater in contact at water temperature for one to three days to reduce the amount of undesirable oil, fats and wastes and suspended solids in the treatment plant.

What is claimed is:

1. A sun screen composition comprising lipase enzyme having the amino acid sequence of SEQ ID NO: 2, triglyceride of natural origin, and antioxidant compound having at least one carboxyl group.

2. The sun screen composition of claim 1, wherein the composition further includes compounds necessary for a spray formulation.

3. The sun screen composition of claim 1, wherein the triglycerides are selected from a group consisting of glycerin, coconut oil, olive oil, and rapeseed oil.

4. The sunscreen composition of claim 1, wherein the antioxidant compound is selected from a group consisting of cinnamic acid; ferulic acid, quinic acid, and shikimic acid.

5. The sunscreen composition of claim 1, wherein the antioxidant is an antioxidant from *Deschampsia antractica*.

6. The sunscreen composition of claim 1, wherein the lipase enzyme is a recombinant protein.

7. The sunscreen composition of claim 6, wherein the lipase enzyme is produced in *Pichia* cells transformed with an expression vector comprising the nucleic acid sequence of SEQ ID NO: 1.

8. A method to produce a sunscreen comprising lipase enzyme having the amino acid sequence of to SEQ ID NO: 2, triglyceride of natural origin, and antioxidant compound having at least one carboxyl group, said method comprising the steps of:
   a) providing an expression vector comprising the nucleic acid sequence of SEQ ID NO:1;
   b) transforming a host cell with the expression vector;
   c) cultivating the host cell and allowing expression of the lipase enzyme
   d) recovering the lipase enzyme, and
   e) using the lipase enzyme for sunscreen production.

9. The method of claim 8, wherein the host cell is *Pichia*.

* * * * *

```
                              SEQUENCE LISTING

<160> NUMBER OF SEQ ID NOS: 9

<210> SEQ ID NO 1
<211> LENGTH: 291
<212> TYPE: DNA
<213> ORGANISM: Deschampsia antarctica

<400> SEQUENCE: 1
atgttcgcca tcaagtacgg cttcgttgcc aaccacacca aatatgggat tgagtggcca      60
ttaatggtgt gctgcgggaa cggcggcccg ccttacaact tcaacccagg aaagtttgga     120
tgcggcgatc tctgcgggcc ggaggcgagg gtgctgagct gggacggtgt gcacttcacc     180
gatttcggca gcggccttgc cgccaagcat gttatgagtg gtgagtactc caagcctaga     240
gtaaagctgg caagcctgat caatggtggc tccaagaaat catcatctct a              291

<210> SEQ ID NO 2
<211> LENGTH: 97
<212> TYPE: PRT
<213> ORGANISM: Deschampsia antarctica

<400> SEQUENCE: 2

Met Phe Ala Ile Lys Tyr Gly Phe Val Ala Asn His Thr Lys Tyr Gly
1               5                   10                  15

Ile Glu Trp Pro Leu Met Val Cys Cys Gly Asn Gly Gly Pro Pro Tyr
20                  25                  30

Asn Phe Asn Pro Gly Lys Phe Gly Cys Gly Asp Leu Cys Gly Pro Glu
35                  40                  45

Ala Arg Val Leu Ser Trp Asp Gly Val His Phe Thr Asp Phe Gly Ser
50                  55                  60

Gly Leu Ala Ala Lys His Val Met Ser Gly Glu Tyr Ser Lys Pro Arg
65                  70                  75                  80

Val Lys Leu Ala Ser Leu Ile Asn Gly Gly Ser Lys Lys Ser Ser Ser
85                  90                  95

Leu

<210> SEQ ID NO 3
<211> LENGTH: 20
<212> TYPE: DNA
<213> ORGANISM: artificial sequence
<220> FEATURE:
<223> OTHER INFORMATION: Primer fw3F9
```

-continued

<400> SEQUENCE: 3
catgttcgcc atcaagtacg                                                                              20

<210> SEQ ID NO 4
<211> LENGTH: 25
<212> TYPE: DNA
<213> ORGANISM: artificial sequence
<220> FEATURE:
<223> OTHER INFORMATION: primer rev3F9

<400> SEQUENCE: 4
tctagagatg atgatttctt ggagc                                                                        25

<210> SEQ ID NO 5
<211> LENGTH: 21
<212> TYPE: DNA
<213> ORGANISM: artificial sequence
<220> FEATURE:
<223> OTHER INFORMATION: 5-AOX1 promoter primer

<400> SEQUENCE: 5
gactggttcc aattgacaag c                                                                            21

<210> SEQ ID NO 6
<211> LENGTH: 101
<212> TYPE: PRT
<213> ORGANISM: Oryza sativa
<220> FEATURE:
<221> NAME/KEY: PEPTIDE
<222> LOCATION: (1)..(101)
<223> OTHER INFORMATION: putative GDSL lipase/acylhydrolase

<400> SEQUENCE: 6

Met Phe Ala Ile Lys Tyr Asp Leu Val Ala Asn His Thr Lys His Gly
1               5                   10                  15

Ile Glu Lys Pro Leu Met Thr Cys Cys Gly His Gly Gly Pro Pro Tyr
            20                  25                  30

Asn Tyr Asp Pro Lys Lys Ser Cys Thr Ala Asn Asp Lys Asp Leu Cys
        35                  40                  45

Lys Leu Gly Glu Lys Phe Ile Ser Trp Asp Gly Val His Phe Thr Asp
    50                  55                  60

Ala Ala Asn Glu Ile Val Ala Ser Lys Val Ile Ser Gly Glu Phe Ser
65                  70                  75                  80

Ile Pro Arg Ile Lys Leu Thr Ala Ser Val Val Arg Pro Lys Lys Ala
                85                  90                  95

Lys Asn Ser Arg Leu
            100

<210> SEQ ID NO 7
<211> LENGTH: 289
<212> TYPE: PRT
<213> ORGANISM: Arabidopsis thaliana
<220> FEATURE:
<221> NAME/KEY: PEPTIDE
<222> LOCATION: (1)..(289)
<223> OTHER INFORMATION: lipase homolog

<400> SEQUENCE: 7

Gly Asp Ser Asn Ser Asp Thr Gly Gly Leu Val Ala Gly Leu Gly Tyr
1               5                   10                  15

Pro Ile Gly Phe Pro Asn Gly Arg Leu Phe Phe Arg Arg Ser Thr Gly
            20                  25                  30

```
Arg Leu Ser Asp Gly Arg Leu Leu Ile Asp Phe Leu Cys Gln Ser Leu
 35                  40                  45

Asn Thr Ser Leu Leu Arg Pro Tyr Leu Asp Ser Leu Gly Arg Thr Asn
 50                  55                  60

Val Ala Asn Phe Ala Ile Ala Gly Ser Ser Thr Leu Pro Lys Asn Val
 65                  70                  75                  80

Pro Phe Ser Leu Asn Ile Gln Val Lys Gln Phe Ser His Phe Lys Ser
 85                  90                  95

Arg Ser Leu Glu Leu Ala Ser Ser Ser Asn Ser Leu Lys Gly Met Phe
100                 105                 110

Ile Ser Asn Asn Gly Phe Lys Asn Ala Leu Tyr Met Ile Asp Ile Gly
115                 120                 125

Gln Asn Asp Ile Ala Ile Arg Gly Asn Ser Tyr Ser Gln Thr Val Lys
130                 135                 140

Leu Ile Pro Gln Ile Ile Thr Glu Ile Lys Ser Ser Ile Lys Arg Leu
145                 150                 155                 160

Tyr Asp Glu Glu Gly Arg Arg Phe Trp Ile His Asn Thr Gly Pro Leu
165                 170                 175

Gly Cys Leu Pro Gln Lys Leu Ser Met Val Lys Ser Lys Asp Leu Asp
180                 185                 190

Gln Leu Gly Cys Leu Val Ser Tyr Asn Ser Ala Ala Thr Leu Glu Leu
195                 200                 205

Asp His Met Cys Glu Glu Leu Arg Thr Glu Leu Arg Asp Ala Thr Ile
210                 215                 220

Ile Tyr Ile Asp Ile Tyr Ala Ile Lys Tyr Ser Leu Ile Ala Asn Ser
225                 230                 235                 240

Asn Gln Tyr Gly Phe Lys Ser Pro Leu Met Ala Cys Cys Gly Tyr Gly
245                 250                 255

Gly Thr Pro Asn Val Lys Ile Thr Cys Gly His Lys Gly Ser Asn Val
260                 265                 270

Cys Lys Glu Gly Ser Arg Phe Ile Ser Trp Asp Gly Ile His Tyr Thr
275                 280                 285

Gly
```

<210> SEQ ID NO 8
<211> LENGTH: 365
<212> TYPE: PRT
<213> ORGANISM: Candida antarctica
<220> FEATURE:
<221> NAME/KEY: PEPTIDE
<222> LOCATION: (1)..(365)
<223> OTHER INFORMATION: lipase A

<400> SEQUENCE: 8

```
Met Arg Val Ser Leu Arg Ser Ile Thr Ser Leu Leu Ala Ala Ala Ala
  1                   5                  10                  15

Thr Ala Val Leu Ala Ala Pro Ala Ala Glu Thr Leu Asp Arg Arg Ala
 20                  25                  30

Ala Leu Pro Asn Pro Tyr Asp Asp Pro Phe Tyr Thr Thr Pro Ser Asn
 35                  40                  45

Ile Gly Thr Phe Ala Lys Gly Gln Val Ile Gln Ser Arg Lys Val Pro
 50                  55                  60

Thr Asp Ile Gly Asn Ala Asn Asn Ala Gln Leu Gln Tyr Arg Thr Thr
 65                  70                  75                  80

Asn Thr Gln Asn Glu Ala Val Ala Asp Val Ala Thr Val Trp Ile Pro
 85                  90                  95
```

```
Ala Lys Pro Ala Ser Pro Pro Lys Ile Phe Ser Tyr Gln Val Tyr Glu
100                 105                 110

Asp Ala Thr Ala Leu Asp Cys Ala Pro Ser Tyr Ser Tyr Leu Thr Gly
115                 120                 125

Leu Asp Gln Pro Asn Lys Val Thr Ala Val Leu Asp Thr Pro Ile Ile
130                 135                 140

Ile Gly Gln Gln Gly Tyr Tyr Val Val Ser Asp His Glu Gly Phe
145                 150                 155                 160

Lys Ala Ala Phe Ile Ala Gly Tyr Glu Glu Gly Met Ala Ile Leu Asp
165                 170                 175

Gly Ile Arg Ala Leu Lys Asn Tyr Gln Asn Leu Pro Ser Asp Ser Lys
180                 185                 190

Val Ala Leu Glu Gly Tyr Ser Gly Gly Ala His Ala Thr Val Trp Ala
195                 200                 205

Thr Ser Leu Ala Glu Ser Tyr Ala Pro Glu Ile Gly Ala Ser His Gly
210                 215                 220

Gly Thr Pro Val Ser Ala Lys Asp Thr Phe Thr Phe Leu Asn Gly Gly
225                 230                 235                 240

Pro Phe Ala Gly Phe Ala Leu Ala Gly Val Ser Gly Leu Ser Leu Ala
245                 250                 255

His Pro Asp Met Glu Ser Phe Ile Glu Ala Arg Leu Asn Ala Lys Gly
260                 265                 270

Gln Arg Thr Leu Lys Gln Ile Arg Gly Arg Gly Phe Cys Leu Pro Gln
275                 280                 285

Val Val Leu Thr Leu Asn Val Phe Ser Leu Val Asn Asp Thr Asn Leu
290                 295                 300

Leu Asn Glu Ala Pro Ile Ala Ser Ile Leu Lys Gln Glu Ile Val Val
305                 310                 315                 320

Gln Ala Glu Ala Ser Tyr Ile Val Ser Val Pro Lys Phe Pro Arg Phe
325                 330                 335

Ile Trp His Ala Ile Pro Asp Glu Ile Val Pro Tyr Gln Pro Ala Ala
340                 345                 350

Thr Tyr Val Leu Glu Gln Cys Ala Lys Gly Ala Asn Ile
355                 360                 365

<210> SEQ ID NO 9
<211> LENGTH: 330
<212> TYPE: PRT
<213> ORGANISM: Candida antarctica
<220> FEATURE:
<221> NAME/KEY: PEPTIDE
<222> LOCATION: (1)..(330)
<223> OTHER INFORMATION: lipase precursor B

<400> SEQUENCE: 9

Met Lys Leu Leu Ser Leu Thr Gly Val Ala Gly Val Leu Ala Thr Cys
1               5                   10                  15

Val Ala Ala Thr Pro Leu Val Lys Arg Leu Pro Ser Gly Ser Asp Pro
20                  25                  30

Ala Phe Ser Gln Pro Lys Ser Val Leu Asp Ala Gly Leu Thr Cys Gln
35                  40                  45

Gly Ala Ser Pro Ser Ser Val Ser Lys Pro Ile Leu Leu Val Pro Gly
50                  55                  60

Thr Gly Pro Gln Ser Phe Asp Ser Asn Trp Ile Pro Leu Ser Thr Gln
65                  70                  75                  80
```

-continued

```
Leu Gly Tyr Thr Pro Cys Trp Ile Ser Pro Pro Phe Met Leu Asn
 85              90              95

Asp Thr Gln Val Asn Thr Glu Tyr Met Val Asn Ala Ile Thr Ala Leu
100             105             110

Tyr Ala Gly Ser Gly Asn Asn Lys Leu Pro Val Leu Thr Trp Ser Gln
115             120             125

Gly Gly Leu Val Ala Leu Thr Phe Phe Pro Ser Ile Arg Ser Lys Val
130             135             140

Asp Arg Leu Met Ala Phe Ala Pro Asp Tyr Lys Gly Thr Val Leu Ala
145             150             155             160

Gly Pro Leu Asp Ala Leu Ala Val Ser Ala Pro Ser Val Trp Gln Gln
165             170             175

Thr Thr Gly Ser Ala Leu Thr Thr Ala Leu Arg Asn Ala Gly Gly Leu
180             185             190

Thr Gln Ile Val Pro Thr Thr Asn Leu Tyr Ser Ala Thr Ile Gln Pro
195             200             205

Gln Val Ser Asn Ser Pro Leu Asp Ser Ser Tyr Leu Phe Asn Gly Lys
210             215             220

Asn Val Gln Ala Gln Ala Val Cys Gly Pro Leu Phe Val Ile Asp His
225             230             235             240

Ala Gly Ser Leu Thr Ser Gln Phe Ser Tyr Val Val Gly Arg Ser Ala
245             250             255

Leu Arg Gly Gln Ala Arg Ser Ala Asp Tyr Gly Ile Thr Asp Cys Asn
260             265             270

Pro Leu Pro Ala Asn Asp Leu Thr Pro Glu Gln Lys Val Ala Ala Ala
275             280             285

Ala Leu Leu Ala Pro Ala Ala Ala Ile Val Ala Gly Pro Lys Gln
290             295             300

Asn Cys Glu Pro Asp Leu Met Pro Tyr Ala Arg Pro Phe Ala Val Gly
305             310             315             320

Lys Arg Thr Cys Ser Gly Ile Val Thr Pro
325             330
```